(12) United States Patent
Rouns et al.

(10) Patent No.: US 7,264,859 B2
(45) Date of Patent: *Sep. 4, 2007

(54) LUBRICIOUS COATING FOR MEDICAL DEVICES

(75) Inventors: Cameron Rouns, South Jordan, UT (US); James Perrault, Vista, CA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 205 days.

This patent is subject to a terminal disclaimer.

(21) Appl. No.: 10/705,751

(22) Filed: Nov. 10, 2003

(65) Prior Publication Data

US 2004/0151930 A1 Aug. 5, 2004

Related U.S. Application Data

(63) Continuation-in-part of application No. 10/325,443, filed on Dec. 19, 2002.

(51) Int. Cl.
*A61M 25/00* (2006.01)
*B32B 1/08* (2006.01)
*B32B 27/08* (2006.01)
*B32B 27/26* (2006.01)
*B32B 27/30* (2006.01)

(52) U.S. Cl. .............................. 428/36.91; 428/424.4; 428/447; 428/520; 428/522; 604/265

(58) Field of Classification Search ............ 428/36.91, 428/424.4, 447, 520, 522; 604/265
See application file for complete search history.

(56) References Cited

U.S. PATENT DOCUMENTS

| | | | |
|---|---|---|---|
| 4,111,922 A | 9/1978 | Beede et al. | |
| 4,210,206 A | 7/1980 | Ely et al. | |
| 4,499,154 A | 2/1985 | James et al. | |
| 4,548,844 A | 10/1985 | Podell et al. | |
| 4,575,476 A | 3/1986 | Podell et al. | |
| 4,667,661 A | 5/1987 | Scholz et al. | |
| 4,717,378 A | 1/1988 | Perrault et al. | |
| 4,774,937 A | 10/1988 | Scholz et al. | |
| 4,856,502 A | 8/1989 | Ersfeld et al. | |
| 4,876,126 A | 10/1989 | Takemura et al. | |
| 4,942,193 A | 7/1990 | Van Buskirk et al. | |

(Continued)

FOREIGN PATENT DOCUMENTS

EP 191471 A1 * 8/1986

(Continued)

OTHER PUBLICATIONS

PCT Search Report for PCT/US03/37049, May 6, 2004.

*Primary Examiner*—Ramsey Zacharia
(74) *Attorney, Agent, or Firm*—Dority & Manning, P.A.

(57) ABSTRACT

Medical devices having at least a portion thereof coated with a lubricious polymer are disclosed. The lubricious polymer can be, for instance, a hydrogel polymer, such as a quaternary amine acrylate polymer. To bond the lubricious polymer to the surface of the medical device, the medical device is first subjected to a solvent and a multi-functional monomer. The solvent causes the multi-functional monomer to become imbibed into the surface of the medical device. Thereafter, a polymer having lubricious properties is polymerized on the surface of the device. The multi-functional monomer reacts with the polymer coating securely affixing the polymer coating to the device.

14 Claims, 1 Drawing Sheet

U.S. PATENT DOCUMENTS

| | | |
|---|---|---|
| 5,069,965 A | 12/1991 | Esemplare |
| 5,081,174 A | 1/1992 | VanBuskirk |
| 5,229,450 A | 7/1993 | Van Buskirk et al. |
| 5,246,012 A | 9/1993 | Strickland |
| 5,264,249 A | 11/1993 | Perrault et al. |
| 5,272,012 A | 12/1993 | Opolski |
| 5,395,666 A | 3/1995 | Brindle |
| 5,405,666 A | 4/1995 | Brindle |
| 5,470,625 A | 11/1995 | Perrault |
| 5,474,768 A | 12/1995 | Robinson |
| 5,509,899 A | 4/1996 | Fan et al. |
| 5,571,219 A | 11/1996 | Gorton |
| 5,611,336 A | 3/1997 | Page et al. |
| 5,693,034 A | 12/1997 | Buscemi et al. |
| 5,742,943 A | 4/1998 | Chen |
| 5,800,685 A | 9/1998 | Perrault |
| 5,993,972 A | 11/1999 | Reich et al. |
| 6,039,940 A | 3/2000 | Perrault et al. |
| 6,045,732 A | 4/2000 | Nakatsuji et al. |
| 6,083,393 A * | 7/2000 | Wu et al. .............. 210/500.35 |
| 6,242,042 B1 | 6/2001 | Goldstein et al. |
| 6,287,285 B1 | 9/2001 | Michal et al. |
| 6,306,514 B1 | 10/2001 | Weikel et al. |
| 6,331,509 B1 | 12/2001 | Heimann et al. |
| 6,345,394 B1 | 2/2002 | Nakamura et al. |
| 6,347,246 B1 | 2/2002 | Perrault et al. |
| 6,509,098 B1 | 1/2003 | Merrill et al. |
| 6,656,517 B2 | 12/2003 | Michal et al. |

FOREIGN PATENT DOCUMENTS

| | | |
|---|---|---|
| WO | WO9206694 A1 | 4/1992 |
| WO | WO9639204 A1 | 12/1996 |
| WO | WO9926683 A1 | 6/1999 |
| WO | WO 0012100 A1 | 3/2000 |
| WO | WO 0061205 A1 | 10/2000 |
| WO | WO 0222186 A1 | 3/2002 |
| WO | WO 02053664 A2 | 7/2002 |
| WO | WO 02053664 A3 | 7/2002 |
| WO | WO 03000116 A2 | 1/2003 |
| WO | WO 03000116 A3 | 1/2003 |

* cited by examiner

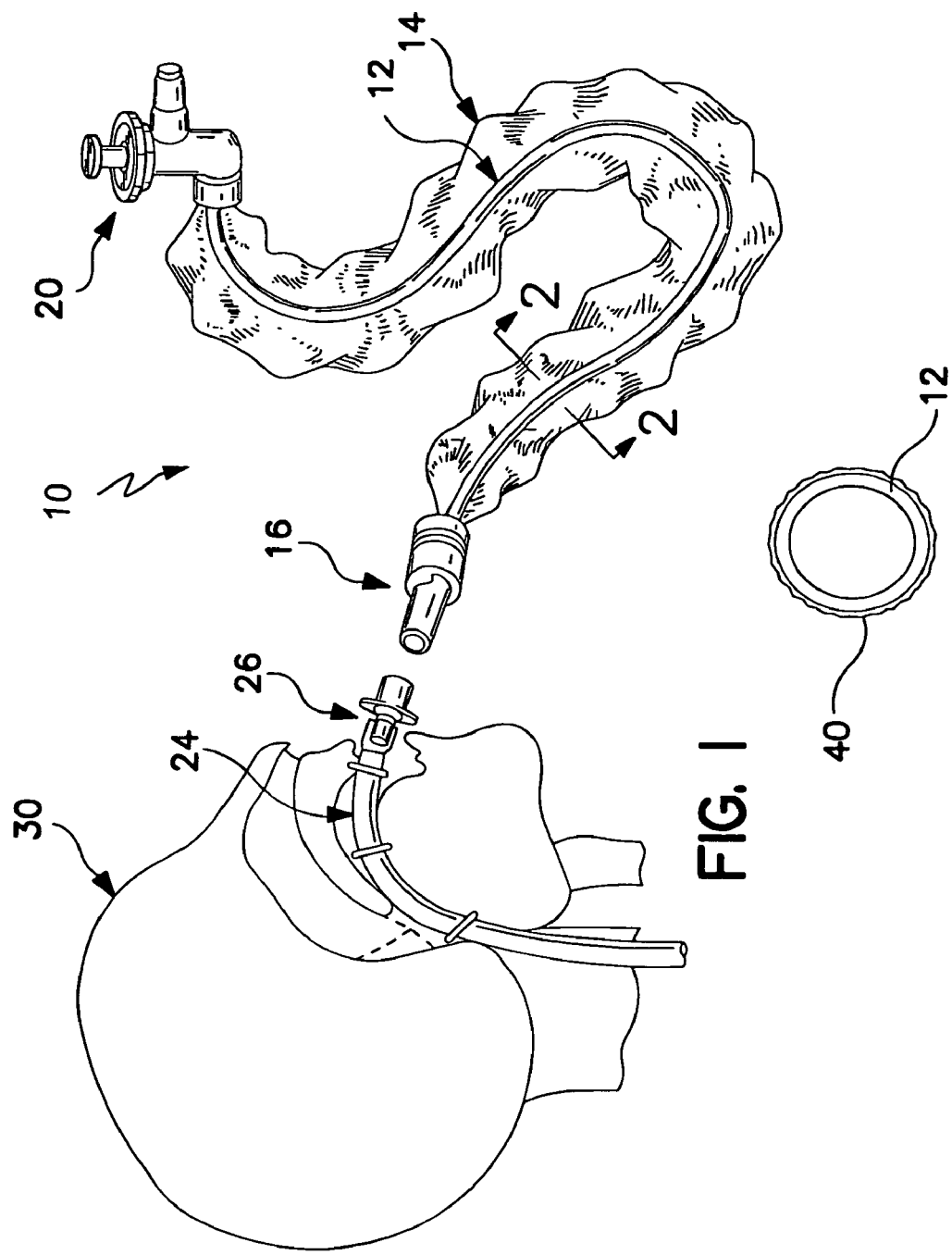

LUBRICIOUS COATING FOR MEDICAL DEVICES

RELATED APPLICATIONS

The present application is a continuation in part of U.S. application Ser. No. 10/325,443, filed on Dec. 19, 2002.

BACKGROUND OF THE INVENTION

Various medical devices are designed to be inserted into a patient to assist in patient care. For example, endotracheal tubes are designed to be inserted through the mouth and throat of a patient for assisting in respiration. Further, other devices, such as tracheal suction devices are used in conjunction with endotracheal tubes to, for instance, remove accumulated secretions from the lungs of a patient.

In addition to being placed in the throat of a patient, other medical devices are designed to be inserted into other areas of the body. For example, coronary angioplasty catheters having an inflatable balloon are inserted and guided through blood vessels. Other types of catheters also are inserted into other areas of the body such as through the stomach walls or in the urinary tract.

During insertion of these types of devices, it can sometimes be difficult to guide the device into a desired location in a patient due to friction between the device and an adjacent surface. Thus, a need exists for a coating that can be applied to a medical device to reduce the coefficient of friction and make the device much easier to insert into a patient. Further, a need exists for a biocompatible and lubricious coating that can be applied to medical devices which also has anti-microbial properties.

SUMMARY OF THE INVENTION

The present invention is generally directed to medical devices having a polymeric portion thereof that has been coated with a lubricious hydrogel polymer. The lubricious coating lowers the coefficient friction of the polymeric portion of the medical device, which facilitates use of the medical device. For example, the lubricious coating makes it easier to insert and guide a medical device into a patient.

In one embodiment, the process of the present invention includes first providing a medical device made from a polymer. For example, the medical device can include a portion made from any suitable thermoplastic or thermoset polymer, such as polyvinyl chloride, a urethane, or a silicone.

A surface of the medical device is then contacted with a solvent and a multi-functional monomer. The solvent causes the multi-functional monomer to be imbibed into the surface of the medical device. For example, in one embodiment, the polymeric surface of the medical device becomes solvated and partially dissolves and/or swells in size. By solvating the surface of the medical device, the multi-functional monomer is capable of either chemically reacting with the surface of the device or forming a mechanical interlock with the surface.

After being contacted with the solvent and the multi-functional monomer, the surface of the medical device is dried. The multifunctional monomer may be partially polymerized if desired.

Next, a hydrogel polymer is polymerized on the surface of the medical device. The hydrogel polymer reacts with the multi-functional monomer imbibed into the surface of the device to form a lubricious coating. For example, in one embodiment, the multi-functional monomer causes the hydrogel monomer to cross-link. Ultimately, the multi-functional monomer serves to bond the hydrogel polymer to the surface of the device.

The multi-functional monomer can be any suitable monomer capable of attaching to the surface of the medical device and also reacting with the hydrogel polymer. The multi-functional monomer can be, for instance, an acrylate (including methacrylates), an acrylamide, a vinyl pyrrolidone, a cationic quaternary ammonium monomer, and the like. When the multi-functional monomer is an acrylate, for instance, the monomer may be a triacrylate, a tetraacrylate, a pentaacrylate, a hexaacrylate, or a diacrylate. The acrylate may be alkoxylated. In one embodiment, for instance, the monomer may be an ethoxylated trimethyolpropane triacrylate.

Any suitable hydrogel polymer can be used in accordance with the present invention. In one embodiment, for instance, the hydrogel polymer is a cationic quaternary amine acrylate polymer. In this embodiment, the hydrogel polymer is polymerized on the surface of the medical device by first contacting the surface of the medical device with a monomer such as an acryloyloxyethyl(or propyl)-trialkyl (or aryl)-substituted ammonium salt or an acrylamidoethyl(or propyl)-trialkyl(or aryl)-substituted ammonium salt. In one embodiment, for instance, the medical device can be dipped into a solution containing the above monomers. Once the monomers are applied to the surface of the medical device, the monomers can be polymerized by, for instance, exposing the medical device to ultraviolet radiation.

Various medical devices can be treated in accordance with the present invention. Such medical devices can include, for instance, tracheal suction devices, endotracheal tubes, catheters, balloons, guidewires, stylets, introducers, and the like.

Of particular advantage, in one embodiment, the lubricious coating can have inherent anti-microbial properties which can serve to further protect the medical device and the patient during use.

Other features and aspects of the present invention are discussed in greater detail below.

BRIEF DESCRIPTION OF THE FIGURES

A full and enabling disclosure of the present invention, including the best mode thereof to one of ordinary skill in the art, is set forth more particularly in the remainder of the specification, including reference to the accompanying figures in which:

FIG. 1 is a perspective view of an endotracheal tube and an aspirating device that may be made in accordance with the present invention;

FIG. 2 is a cross-sectional view of the catheter tube that forms part of the aspirating device shown in FIG. 1.

Repeated use of reference characters in the present specification and drawings is intended to represent the same or analogous features or elements of the present invention.

DETAILED DESCRIPTION OF THE INVENTION

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or the spirit of the invention. For instance, features illustrated or described as part of one embodiment can be used on another embodiment to yield still a further embodiment. Thus, it is intended that the present invention cover such modifications and variations as come within the scope of the appended claims and their equivalents.

In general, the present invention is directed to a lubricious coating that can be applied to medical devices. The medical devices that can be treated in accordance with the present invention include, but are not limited to, devices that are typically inserted into the body of a patient and other devices where low friction surfaces are desired. By way of example, medical devices that can include a lubricious coating made according to the present invention include tracheal devices, such as endotracheal tubes, aspirating devices and other tracheal suction devices, bronchoalveolar lavage catheters, enternal feeding devices, urinary catheters, catheters used in coronary angioplasty, guidewires, stylets, introducers, and the like. The lubricious coating of the present invention is particularly designed to be applied to polymeric surfaces that may be contained within the medical device.

Once applied to a medical device, the lubricious coating of the present invention lowers the coefficient of friction and facilitates insertion of the device into a patient. Depending upon the medical device treated in the application, the lubricious coating can also serve to protect the medical device and/or the patient during use of the medical device. Of particular advantage, in one embodiment, the lubricious coating of the present invention can have anti-microbial properties which further serve to protect patients.

The lubricious coating of the present invention is generally a polymer. For example, the polymer can be a cationic quaternary amine acrylate hydrogel polymer. According to the present invention, the polymer is bonded to a surface of a medical device by first imbibing a multi-functional monomer into the surface of the device. As used herein, the term "imbibing" means that the multi-functional monomer is either chemically or mechanically bonded to a polymeric surface. Further, the term "monomer" means any material capable of polymerizing or cross-linking with a polymer and can include monomers, oligomers, polymers, and the like.

Once the multi-functional monomer is bonded to the surface of the medical device, the surface is contacted with a prepolymer, such as a hydrogel prepolymer. Polymerization is then initiated causing the prepolymer to form into a hydrogel polymer coating. During polymerization, the hydrogel polymer reacts with the multi-functional monomer. For instance, in one embodiment, the multi-functional monomer cross-links with the hydrogel polymer. In this manner, the multi-functional monomer becomes part of the hydrogel polymer structure while simultaneously attaching the hydrogel polymer to the surface of the medical device. Ultimately, a lubricious coating is formed on the surface of the medical device that is securely affixed to the device.

For purposes of illustration, FIG. 1 shows an endotracheal tube 24 in conjunction with an aspirating device 10 that can both be made in accordance with the present invention. The endotracheal tube 24 is shown placed in the mouth and throat of a patient 30. In this embodiment, the endotracheal tube 24 includes a fitting 26 which is adapted to engage a respirating device or, alternatively, the aspirating device 10 as shown in FIG. 1.

The aspirating device 10 includes an aspirating catheter tube 12 which extends along substantially the entire axial length of the device. The catheter tube 12 is encased within a tubular sleeve or envelope 14 of a flexible film made from a polymer, such as medical grade polyethylene.

At one end of the aspirating device 10 is a manually operable valve 20. The valve 20 is configured to be connected to a vacuum source during use. The valve 20 can be used to control the amount of suction present in the catheter tube when removing secretions from a patient's lungs.

At the opposite end of the aspirating device 10 is a fitting 16 configured to attach to the endotracheal tube 24. In this embodiment, the fitting 16 covers the exposed end of the catheter tube 12 to accommodate a sterile insertion and retraction of the catheter tube 12 into the fitting 26 located at the end of the endotracheal tube 24. The fitting 16 may be welded or bonded into place at the end of the tubular sleeve 14.

When the aspirating device is being used, the catheter tube 12 is manually manipulated through the endotracheal tube 24 into the lungs. The envelope 14 surrounding the catheter tube 12 collapses as the catheter tube is inserted into the patient. Once positioned in the lungs, the catheter tube 12 is used to clear secretions from the patient's airway.

In accordance with the present invention, the endotracheal tube 24 and the catheter tube 12 can be treated with the lubricious coating which facilitates placement of the medical devices within the patient. For example, FIG. 2 shows a cross-section of the catheter tube 12. As shown, the catheter tube 12 includes a coating 40 applied to the exterior surface of the catheter tube. In accordance with the present invention, the coating 40 is lubricious and can be made from a hydrogel polymer that is securely affixed to the surface of the catheter tube. The catheter tube can be made from a polymer, such as polyvinyl chloride, a urethane, a silicone, and the like. By applying the coating 40 to the catheter tube 12, the coefficient of friction of the outside surface of the catheter tube is reduced, which in turn lowers the resistance that is experienced when the catheter tube is being inserted through the endotracheal tube 24.

In addition to coating the outside surface of the catheter tube, the inside of the catheter tube can also be treated in accordance with the present invention. Further, the inside and outside surfaces of the endotracheal tube 24 can also be treated as desired.

In addition to the endotracheal tube 24 and the catheter 12 shown in FIG. 1, it should be understood that the lubricious coating of the present invention can be applied to various other medical devices as well. In general, any polymeric part of a medical device where a lower coefficient of friction is desired can be coated in accordance with the present invention.

One embodiment of a process for coating a medical device in accordance with the present invention will now be described in detail. As discussed above, the present invention is generally directed to applying a coating of a quaternary amine acrylate hydrogel polymer to the surface of a medical device. In forming the hydrogel coating, a surface of the medical device is first contacted with a multi-functional monomer. As used herein, "medical device" means a complete device or any part or component thereof. For example, in many applications, a part for a medical device will be treated in accordance with the present invention and then later assembled into the device.

The medical device can be made from any suitable thermoplastic or thermoset polymer capable of forming a mechanical or chemical attachment to the multi-functional monomer. Suitable polymers include, for instance, silicones and urethanes. In one particular embodiment, for instance, the medical device can be made from polyvinyl chloride.

In order to attach the multi-functional monomer to the surface of the polymeric medical device, the medical device is also contacted with a solvent that is capable of solvating or swelling the polymer. The solvent and the multi-functional monomer can be first combined together and then contacted with the medical device or can contact the medical device sequentially. In one embodiment, the solvent partially dissolves the surface of the medical device or otherwise causes the polymeric surface to swell. During swelling and partially dissolving, the multi-functional monomer can form a mechanical interlock with the surface. In other embodiments, the multi-functional monomer can also undergo a chemical reaction with the surface of the polymer.

Various solvents can be used in accordance with the present invention. Such solvents include, for instance, dimethylsulfoxide (DMSO), acetone, alcohols, methylethyl ketone, toluene, xylene, N,N-dimethyl formamide (DMF), tetrahydrofuran and the like. The particular solvent chosen for an application will depend upon the type of polymer being coated and the type multi-functional monomer used.

For example, when the medical device contains polyvinyl chloride, the solvent may be DMSO and ketones. If the medical device contains a urethane, however, the solvent may be DMF or tetrahydrofuran. If the medical device contains silicone, the solvent chosen may be toluene or xylene.

The multi-functional monomer used in the present invention should be capable of mechanically or chemically bonding to the surface of the medical device and later reacting with the hydrogel polymer that is formed on the surface of the medical device. For example, a multi-functional monomer can be used that will cause cross-linking in a quaternary amine acrylate hydrogel polymer.

The multi-functional monomer can be, for instance, an acrylate such as a cationic quaternary ammonium monomer, other ammonium compounds, an acrylamide, or a vinyl pyrrolidone. The multi-functional monomer may be bifunctional, trifunctional, tetrafunctional, pentafunctional, or hexafunctional.

Difunctional monomers which may be used in the present invention include butylene glycol diacrylate, butylene glycol dimethacrylate, butanediol diacrylate, butanediol dimethacrylate, hexanediol diacrylate, hexanediol dimethacrylate, aliphatic dimethacrylate monomer, alkoxylated aliphatic diacrylate, alkoxylated cyclohexane dimethanol diacrylate, alkoxylated hexanediol diacrylate, alkoxylated neopentyl glycol diacrylate, aromatic dimethacrylate monomer, caprolactione modified neopentylglycol hydroxypivalate diacrylate, cyclohexane dimethanol diacrylate, cyclohexane dimethanol dimethacrylate, diethylene glycol diacrylate, diethylene glycol dimethacrylate, dipropylene glycol diacrylate, ethoxylated (10) bisphenol a diacrylate, ethoxylated (2) bisphenol a dimethacrylate, ethoxylated (3) bisphenol a diacrylate, ethoxylated (30) bisphenol a diacrylate, ethoxylated (30) bisphenol a dimethacrylate, ethoxylated (4) bisphenol a diacrylate, ethoxylated (4) bisphenol a dimethacrylate, ethoxylated (8) bisphenol a dimethacrylate, ethoxylated bisphenol a dimethacrylate, ethoxylated bisphenol a dimethacrylate, ethoxylated (10) bisphenol dimethacrylate, ethoxylated (6) bisphenol a dimethacrylate, ethylene glycol dimethacrylate, hydroxypivalaldehyde modified trimethylolpropane diacrylate, neopentyl glycol diacrylate, neopentyl glycol dimethacrylate, polyethylene glycol (200) diacrylate, polyethylene glycol (400) diacrylate, polyethylene glycol (400) dimethacrylate, polyethylene glycol (600) diacrylate, polyethylene glycol (600) dimethacrylate, polyethylene glycol dimethacrylate, polypropylene glycol dimethacrylate, propoxylated (2) neopentyl glycol diacrylate, tetraethylene glycol diacrylate, tetraethylene glycol dimethacrylate, triethylene glycol diacrylate, triethylene glycol dimethacrylate, tripropylene glycol diacrylate, and the like. The above difunctional monomers are all available from the Sartomer Company, Inc. of Exton, Pa.

Trifunctional monomers that may be used in the present invention include ethoxylated (15) trimethylolpropane triacrylate, ethoxylated (3) trimethylolpropane triacrylate, ethoxylated (6) trimethylolpropane triacrylate, ethoxylated (9) trimethylolpropane triacrylate, ethoxylated (20) trimethylolpropane triacrylate, highly propoxylated (5.5) glyceryl triacrylate, low viscosity trimethylolpropane triacrylate, pentaerythritol triacrylate, propoxylated (3) glyceryl triacrylate, propoxylated (3) trimethylolpropane triacrylate, propoxylated (6) trimethylolpropane triacrylate, trimethylolpropane triacrylate, trimethylolpropane trimethacrylate, tris (2-hydroxy ethyl)isocyanurate triacrylate, and the like. The above trifunctional monomers are all available from the Sartomer Company, Inc. of Exton, Pa.

Tetrafunctional, pentafunctional and hexafunctional monomers that may be used in the present invention include di-trimethylolpropane tetraacrylate, dipentaerythritol pentaacrylate, ethoxylated (4) pentaerythritol tetraacrylate, low viscosity dipentaerythritol pentaacrylate, pentaacrylate ester, pentaerythritol tetraacrylate, caprolactone modified dipentaerythritol hexaacrylate, and the like. The above monomers are all available from the Sartomer Company, Inc. of Exton, Pa.

All of the above listed monomers are acrylates. As shown above, the acrylates may be alkoxylated using, for instance, ethoxylate groups or propoxylate groups. Other acrylates include cationic quaternary ammonium monomers. Examples of cationic quaternary ammonium monomers include N,N-Dimethylaminoethyl acrylate DMS (dimethyl sulfate), N,N-Dimethylaminoethyl acrylate MC (methyl chloride), N,N-Dimethylaminoethyl methacrylate DMS, N,N-Dimethylaminoethyl methacrylate MC, or Diallyldimethylammonium chloride, which are all commercially available from Ciba Specialty Chemicals. Other quaternary ammonium monomers that may be used include acryloxethyldimethyl benzyl ammonium chloride, acryloxyethyltrimethyl ammonium chloride, methacryloxyethyldimethyl benzyl ammonium chloride, or methacryloxyethyltrimethyl ammonium chloride, which may be obtained commercially from Atofina.

Other examples of multi-functional monomers that can be used in the present invention include methylene-bis-acrylamide (MBA) and diethylene glycol diacrylate, which are both commercially available from Polysciences, Inc., Warrington, Pa. Additional examples of multi-functional monomers which may be acceptable for use in the present invention include ethylene glycol diacrylate, triethylene glycol-bis-methacrylate, ethylene glycol-bis-methacrylate, ethylene glycol-dimethacrylate, bisacrylamide, triethyleneglycol-bis-acrylate, 3,3'-ethylidene-bis (N-vinyl-2-pyrrolidone), trimethylolpropane trimethacrylate, glycerol trimethacrylate, polyethylene glycol dimethacrylate, and other polyacrylate and polymethacrylate esters.

In addition to the solvent and the multi-functional monomer, the surface of the medical device can also be contacted with an initiator. If needed, the initiator can be used to initiate polymerization of the hydrogel polymer that is to be formed on the surface.

Examples of initiators which may be used include, for example, IRGACURE® 184 (1-hydroxycyclohexyl phenyl ketone), and DAROCURE® 1173 (α-hydroxy-1, αdimethylacetophenone) which are both commercially available from Ciba-Geigy Corp. These UV catalysts are desired in some applications because they are non-yellowing. Additional examples of initiators (which may be photo initiators or thermal initiators) may include benzoyl peroxide, azo-bis-isobutyro-nitrile, di-t-butyl peroxide, bromyl peroxide, cumyl peroxide, lauroyl peroxide, isopropyl percarbonate, methylethyl ketone peroxide, cyclohexane peroxide, t-butylhydroperoxide, di-t-amyl peroxide, dicymyl peroxide, t-butyl perbenzoate, Benzoin alkyl ethers (such as benzoin, benzoin isopropyl ether, and benzoin isobutyl ether), benzophenones (such as benzophenone and methyl-o-benzoyl benzoate), acetophenones (such as acetophenone, trichloro-acetophenone, 2,2-diethoxyacetophenone, p-t-butyl-trichloro-acetophenone, 2,2-dimethoxy-2-phenylacetophenone, and p-dimethylaminoacetophenone), thioxanthones (such as xanthone, thioxanthone, 2-chlorothioxanthone, and 2-isopropyl thioxanthone), benzyl 2-ethyl anthraquinone, methylbenzoyl formate, 2-hydroxy-2-methyl-1-phenyl propane-1-one, 2-hydroxy-4'-isopropyl-2-methyl propiophenone, e-hydroxy ketone, tet-remethyl thiuram monosulfide, allyl diazonium salt, and a combination of camphorquinone or 4-(N,N-dimethylamino)benzoate.

The medical device may be contacted with a solution comprised of one or more of the following components: a solvent, a multi-functional monomer, and an initiator, or the medical device may be contacted with the separate components in sequential steps. In one particular embodiment, a solution can be formed containing the solvent, the multi-functional monomer, and the initiator. The multi-functional monomer can be present in the solution in an amount from about 5% to about 50% by weight. The initiator can be present in the solution in an amount from about 0.05% to about 5.0% by weight. The medical device can be contacted with the solution, such as being dipped in the solution. In particular, the surface of the medical device can be contacted with the solution in an amount of time sufficient for the polymeric surface to either swell and/or partially dissolve. For example, the surface of the medical device optionally may be contacted with solution at room temperature for about 30 seconds to about 3 minutes.

If contacted with the solution, the medical device may be dried if desired although this step is not necessary. For instance, the medical device can be heated or can simply be air dried. In this manner, the multi-functional monomer becomes imbibed into the surface of the polymer.

Also optional, polymerization may be initiated in a portion of the multi-function monomer. Partially polymerizing the multi-functional monomer may serve to create a better interlock with the surface of the medical device. Further, only a portion of the multi-functional monomer may be polymerized in order to leave active functional sites remaining. In some embodiments, it should be understood that partial polymerization of the multi-functional monomer may not be necessary.

Once the multi-functional monomer is imbibed into the surface of the medical device and mechanically or chemically attached to the medical device, the surface of the medical device is then contacted with a monomer or pre-polymer capable of forming the hydrogel polymer. In one embodiment, the hydrogel polymer that is formed on the surface of the medical device is a cationic quaternary amine acrylate polymer. For example, the hydrogel polymer can comprise the following:

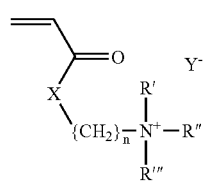

FORMULA I wherein n is an integer of 2 to 3; R', R" and R'" are independently selected from the group consisting of H, $C_1$ to $C_{16}$ alkyl, aryl, arylamine, alkylamine, alkaryl and aralkyl; X is selected from the group consisting of O and NH; and $Y^-$ is an acceptable anionic counterion to the $N^+$ of the quaternary amine.

Alkyl groups may be lower alkyl, of C1, to C8 with methyl or ethyl groups being particularly desired. Aryl is desireably phenyl but can be any suitable aromatic moiety such as those selected from the group consisting of phenyl, thiophenyl, naphthyl, biphenyl, pyridyl, pyrimidinyl, pyrazyl, pyridazinyl, furyl, thienyl, pyrryl, quinolinyl and bipyridyl and the like. Representative of an aralkyl grouping is benzyl and representative of an alkaryl grouping is tolyl. X is desireably O or NH. Representative of counterions represented by $Y^-$ are members selected from the group consisting of $Cl^-$, $Br^-$, $HSO_4^-$, and $CH_3SO_4^-$ with $Cl^-$ being particularly desired. Alkyl groups can be straight or branched chained and alkyl and aryl groups can be substituted by non-interfering substituents that do not obstruct with the functionality of the polymers.

Monomers or pre-polymers that can be used to form the above hydrogels include the following:

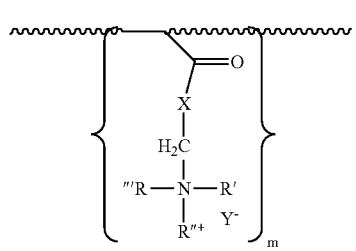

FORMULA II where R', R" and R'", X, Y— have the meanings given above in Formula I and m is an integer greater than 50,000. Polymerization is brought about by methods known in the art such as free radical curing with an initiator induced polymerization in the presence of water by ultra-violet curing and a multi-functional cross-linking agent or by anionic 1,2 alkoxy anion induced polymerization.

Examples of specific quaternary amine cationic acrylate ester or amide monomers that may be polymerized are shown in following Formulas II, IV, V and IV.

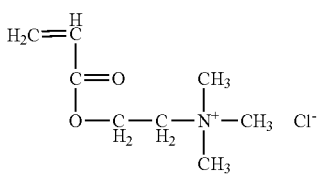

FORMULA III

Formula III shows acryloyloxyethyltrimethyl ammonium chloride which is available from CPS Chemical Co.

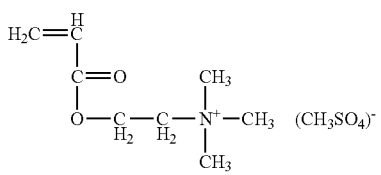

FORMULA IV

Formula IV shows acryloyloxyethyltrimethyl ammonium methyl sulfate which is available from Allied Colloid Co.

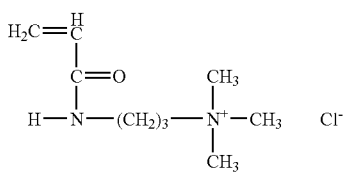

FORMULA V

Formula V shows acrylamidopropyltrimethyl ammonium chloride which is available from Stockhausen (Germany).

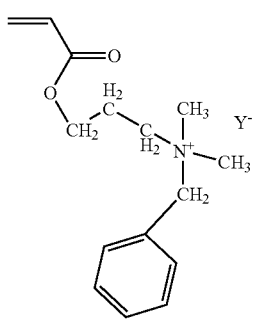

FORMULA VI

Formula VI shows acryloxyethyldimethylbenzyl ammonium chloride which is available from Elf Atochem. As shown in the above formula, $Y^-$ may be represented by the counterion chloride.

Various methods can be used to apply the monomer to the surface of the medical device. For instance, in one embodiment, the monomer can be combined with water and sprayed onto the medical device. In another embodiment, the medical device can be dipped into a solution containing the monomer. For example, in one embodiment, the monomer can be present in the solution in an amount from about 50% to about 98% by weight, particularly from about 70% to about 90% by weight, and applied to the surface of the medical device.

The viscosity of the monomer solution can be adjusted depending upon the particular application and circumstances. In general, when dipping the medical device into the solution, higher viscosities will cause more of the monomer to remain on the surface of the device. Thus, if thicker coatings are desired, the viscosity can be increased. The viscosity of the solution can be increased by minimizing the amount of water in the solution. Additionally, thickeners, such as a polyacrylamide, can be added to the solution. The viscosity of the solution can also be increased by partially polymerizing the monomer.

In addition to the monomer and a thickener, the solution can contain other various ingredients. For instance, if desired, an initiator as described above can also be contained within the monomer solution. Further, if desired more of the multi-functional monomer can also be combined with the monomer and applied to the surface of the medical device.

Once the monomer has been applied to the medical device, the monomer is polymerized to form the hydrogel polymer. During polymerization, the monomer also reacts with the multi-functional monomer previously applied to the medical device. For example, in one embodiment, the multi-functional monomer causes the hydrogel to cross-link.

Polymerization of the polymer can be initiated in various ways. In general, the manner in which the hydrogel polymer is polymerized depends upon the particular initiator chosen. For example, polymerization of the polymer can occur when the monomer is exposed to light energy, heat or to a particular chemical agent.

In one embodiment, polymerization of the monomer to form the hydrogel polymer is caused by exposing the medical device to ultraviolet light. The ultraviolet light may be, for instance, non-ionizing and can have a wavelength of at least about 200 nanometers. For example, in one embodiment, after the monomer is applied to the medical device, the medical device can be exposed to one or more 600-watt ultraviolet lamps. For example, in one embodiment, circular xenon lamps can be used. The medical device may be exposed to the ultraviolet rays until the hydrogel polymer is cured.

Upon curing, the hydrogel polymer becomes bonded to the medical device through reaction with the multi-functional monomer. The hydrogel polymer lowers the coefficient of friction on the surface of the medical device and provides a lubricious coating. Further, in some embodiments, the hydrogel polymer can also possess anti-microbial properties which can be particularly advantageous in medical applications.

The thickness of the hydrogel polymer on the medical device can depend on the particular application. For most embodiments, however, the thickness of the coating will be from about 0.1 to about 10 mils hydrated. In order to produce thicker coatings, in some embodiments, the medical device can be dipped into the monomer multiple times. The monomer can be polymerized and cured in between each dipping step or can be polymerized and cured all in a single step.

If desired, in some embodiments, after the hydrogel polymer is polymerized the medical device can also be soaked in an aqueous solution, such as a saline solution, to remove any residual monomer.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A medical device comprising:
a surface configured to move in relation to an adjacent surface; and
a lubricious coating applied to the surface, the lubricious coating comprising a quaternary amine acrylate hydrogel polymer that has been cross-linked to a multi-functional monomer, the multi-functional monomer having been imbibed into the surface of the medical device, the multi-functional monomer comprising an acrylate or an ammonium compound.

2. A medical device as defined in claim 1, wherein the surface of the device is made from a thermoplastic or a thermoset.

3. A medical device as defined in claim 1, wherein the surface of the device is made from polyvinyl chloride.

4. A medical device as defined in claim 1, wherein the quaternary amine acrylate hydrogel polymer is formed from a monomer having the structure:

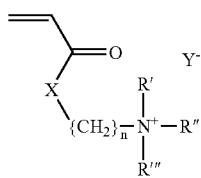

wherein n is an integer of 2 to 3; R', R" and R''' are independently selected from the group consisting of H, $C_1$ to $C_{16}$ alkyl, aryl, arylamine, alkylamine, alkaryl and aralkyl; X is selected from the group consisting of O and NH; and $Y^-$ is an acceptable anionic counterion to the $N^+$ of the quaternary amine.

5. A medical device as defined in claim 1, wherein the medical device comprises tracheal suction device, a catheter, a guidewire, a stylet, an enteral feeding device, an introducer, or an endotracheal tube.

6. A medical device as defined in claim 1, wherein the surface of the device is made from a silicone or a urethane.

7. A medical device as defined in claim 1, wherein the quaternary amine acrylate hydrogel polymer comprises acryloyloxyalkyl-trialkyl-substituted ammonium salt, an acryloyloxyalkyl-aryl-substituted ammonium salt, an acrylamidoalkyl-trialkyl-substituted ammonium salt, or an acrylamidoalkyl-aryl-substituted ammonium salt.

8. A medical device as defined in claim 1, wherein the quaternary amine acrylate hydrogel polymer comprises acryloyloxyethyltrimethyl ammonium chloride, or acryloyloxyethyltrimethyl ammonium methyl sulfate.

9. A medical device as defined in claim 1 wherein the multi-functional monomer comprises an alkoxylated acrylate.

10. A medical device as defined in claim 1 wherein the multi-functional monomer comprises a triacrylate.

11. A medical device as defined in claim 1, wherein the multi-functional monomer comprises a tetraacrylate, a pentaacrylate, a hexaacrylate, or a diacrylate.

12. A medical device as defined in claim 1, wherein the multi-functional monomer comprises an ethoxylated trimethylolpropane triacrylate, a propoxylated glyceryl triacrylate, trimethylolpropane triacrylate, pentaerythritol triacrylate, a propoxylated glyceryl triacrylate, a propoxylated trimethylolpropane triacrylate, trimethylol propane trimethacrylate, tris (2-hydroxy ethyl) isocyanurate triacrylate, di-trimethylolpropane tetraacrylate, dipentaerythritol pentaacrylate, an ethoxylated pentaerythritol tetraacrylate, a dipentaerythritol pentaacrylate, a pentaacrylate ester, pentaerythritol tetraacrylate, or a caprolactone modified dipentaerythritol hexaacrylate.

13. A medical device as defined in claim 1, wherein the multi-functional monomer comprises N,N-Dimethylaminoethyl acrylate dimethylsulfate, N,N-Dimethylaminoethyl acrylate methylchloride, N,N-Dimethylaminoethyl methacrylate dimethylsulfate, N,N-Dimethylaminoethyl methacrylate methylchloride, Diallyldimethylammonium chloride, acryloxyethyldimethyl benzyl ammonium chloride, acryloxyethyltrimethyl ammonium chloride, methacryloxyethyldimethyl benzyl ammonium chloride, or methacryloxyethyltrimethyl ammonium chloride.

14. A medical device as defined in claim 1, wherein the multi-functional monomer comprises an ethoxylated trimethylolpropane triacrylate.

* * * * *